(12) United States Patent
Onuki et al.

(10) Patent No.: US 10,458,923 B2
(45) Date of Patent: Oct. 29, 2019

(54) PRINT DATA PROCESSING METHOD, PRINT DATA PROCESSING DEVICE, AND RECORDING MEDIUM HAVING RECORDED THEREIN PRINT DATA PROCESSING PROGRAM

(71) Applicant: SCREEN HOLDINGS CO., LTD., Kyoto (JP)

(72) Inventors: Yohei Onuki, Kyoto (JP); Kenichi Yokouchi, Kyoto (JP); Hiroyuki Segawa, Kyoto (JP)

(73) Assignee: SCREEN HOLDINGS CO., LTD., Kyoto (JP)

( * ) Notice: Subject to any disclaimer, the term of this patent is extended or adjusted under 35 U.S.C. 154(b) by 0 days.

(21) Appl. No.: 15/870,759

(22) Filed: Jan. 12, 2018

(65) Prior Publication Data
US 2018/0246041 A1 Aug. 30, 2018

(30) Foreign Application Priority Data
Feb. 24, 2017 (JP) .................................. 2017-032884

(51) Int. Cl.
*G06K 1/00* (2006.01)
*G01N 21/892* (2006.01)
(Continued)

(52) U.S. Cl.
CPC ..... *G01N 21/8921* (2013.01); *B41F 33/0036* (2013.01); *G06F 3/1202* (2013.01); *G06K 15/186* (2013.01); *G06K 15/408* (2013.01); *G06T 7/0004* (2013.01); *G06T 2207/10024* (2013.01); *G06T 2207/30144* (2013.01)

(58) Field of Classification Search
None
See application file for complete search history.

(56) References Cited

U.S. PATENT DOCUMENTS 5,835,629 A * 11/1998 Seo ...................... G06K 9/4638
382/173
8,203,761 B2 * 6/2012 Arima .................. H04N 1/4097
358/3.26
(Continued)

FOREIGN PATENT DOCUMENTS

JP 2012-061759 A 3/2012
JP 2014019016 A 2/2014

*Primary Examiner* — Dung D Tran
(74) *Attorney, Agent, or Firm* — McDermott Will & Emery LLP

(57) ABSTRACT

A method for processing print data includes a matching processing step of performing pattern matching between a streak detection pattern including a streak pattern having a width of one pixel and print data after a RIP process, a length measurement step of determining, when matching is established in the matching processing step, a length of a streak candidate part including a part corresponding to the streak pattern in a region where matching is established and a part continuous in an extending direction of the streak pattern and having a same value as a data value of the streak pattern, in the print data, and a determination step of determining whether or not the streak candidate part is white streak data that possibly results in a streak, by comparing the length determined in the length measurement step against a predetermined threshold.

6 Claims, 20 Drawing Sheets

(51) Int. Cl.
    *G06F 3/12*       (2006.01)
    *G06K 15/00*    (2006.01)
    *G06K 15/02*    (2006.01)
    *B41F 33/00*    (2006.01)
    *G06T 7/00*       (2017.01)

(56) References Cited

U.S. PATENT DOCUMENTS

| | | | |
|---|---|---|---|
| 8,548,204 B2 * | 10/2013 | Ikubo | G06K 9/03 358/453 |
| 2012/0069356 A1 | 3/2012 | Kubo et al. | |
| 2012/0206756 A1 * | 8/2012 | Nakashio | H04N 1/00015 358/1.14 |
| 2015/0178902 A1 * | 6/2015 | Lee | B60S 1/0818 382/104 |
| 2017/0177962 A1 * | 6/2017 | Yamazaki | B41J 29/46 |
| 2017/0274690 A1 * | 9/2017 | Ukishima | B41J 29/38 |

* cited by examiner

Fig.9
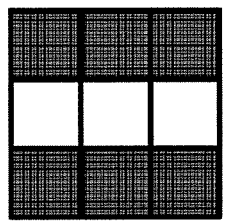
Fig.10
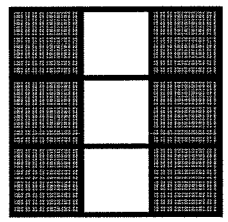
Fig.11
| | | | | | | |
|---|---|---|---|---|---|---|
| (1, 1) | (2, 1) | (3, 1) | (4, 1) | (5, 1) | (6, 1) | ····· |
| (1, 2) | (2, 2) | (3, 2) | (4, 2) | (5, 2) | (6, 2) | ····· |
| (1, 3) | (2, 3) | (3, 3) | (4, 3) | (5, 3) | (6, 3) | ····· |
| (1, 4) | (2, 4) | (3, 4) | (4, 4) | (5, 4) | (6, 4) | ····· |
| (1, 5) | (2, 5) | (3, 5) | (4, 5) | (5, 5) | (6, 5) | ····· |
| (1, 6) | (2, 6) | (3, 6) | (4, 6) | (5, 6) | (6, 6) | ····· |
| ⋮ | ⋮ | ⋮ | ⋮ | ⋮ | ⋮ | |
64

Fig.12

WHITE STREAK DATA

| START COORDINATES | END COORDINATES | LENGTH | DIRECTION |
|---|---|---|---|

Fig.13

| START COORDINATES | END COORDINATES | LENGTH | DIRECTION |
|---|---|---|---|
| (10, 20) | (50, 20) | 40 | 0 |
| (25, 92) | (85, 92) | 60 | 0 |
| (30, 15) | (30, 85) | 70 | 1 |
| ⋮ | ⋮ | ⋮ | ⋮ |

BEFORE CORRECTION → AFTER CORRECTION

←Lu
←Lt
←Ld 72  70  71

←Lu
←Lt
←Ld 74  70  73

| $\frac{1}{8}$ | $\frac{2}{8}$ | $\frac{1}{8}$ |
|---|---|---|
|  | Pt |  |
| $\frac{1}{8}$ | $\frac{2}{8}$ | $\frac{1}{8}$ |

←Lu
←Lt
←Ld

PRINT DATA PROCESSING METHOD, PRINT DATA PROCESSING DEVICE, AND RECORDING MEDIUM HAVING RECORDED THEREIN PRINT DATA PROCESSING PROGRAM

BACKGROUND OF THE INVENTION

Field of the Invention

The present invention relates to a method of processing data for printing (print data processing method), and more particularly, to a method of detecting white streak data occurring due to a fault in a RIP process and of correcting the same.

Description of Related Art

In a plate-making/printing system, first, an edit process using characters, parts (logo, picture, illustration, etc.) and the like constituting a print material is performed by using a computer (such as a personal computer) called a front-end, and page data describing a print target by page description language or the like is generated. Next, a RIP process is performed on the page data. In this RIP process, a rasterization process (rendering process) is performed after an interpretation process of analyzing the position or the like of each object, and multi-valued bitmap data is thereby generated, and then, halftone dot data (binary bitmap data) is generated by performing a halftone dot meshing process (screening process) on the multi-valued bitmap data. Then, a printing plate is made by a plate-making device using the halftone dot data. Thereafter, printing is performed by a printer using the printing plate. Alternatively, the halftone dot data is transmitted to a digital printer, and printing based on the halftone dot data is performed by the digital printer.

Following prior art documents are known in relation to the present invention. Japanese Laid-Open Patent Publication No. 2012-61759 discloses an invention of an image forming device which is capable of continuing printing even when an error occurs during printing. The image forming device is provided with a conversion unit configured to perform a re-RIP process based on a fixing print condition, which is a print condition for fixing an error. For example, when an error occurs due to setting of a sheet size, a re-RIP process according to the sheet size by which the error is fixed is performed, and printing is performed based on data after the re-RIP process. Furthermore, Japanese Laid-Open Patent Publication No. 2014-19016 discloses an invention of a printing system which is capable of detecting a fault occurring in an upstream process. This printing system is provided with a check unit configured to compare image data for comparison generated based on data before a RIP-process and image capturing data capturing a printing result which is based on image data for printing after the RIP process. A fault which has occurred in an upstream process is detected by the check unit extracting a difference between the image data for comparison and the image capturing data.

As described above, in a plate-making/printing system, the RIP process of performing a rasterization process on data in a vector format is performed before fabrication of a printing plate at a plate-making device or printing at a digital printer, for example. However, data of a white streak (hereinafter referred to as "white streak data") having a width of one pixel may occur in data after the RIP process, due to various factors such as transparency effect, rotation, imposition, and the pattern of an image. For example, as indicated by an arrow 90 in FIG. 35, a part which is supposed to be painted is not painted. This part is the white streak data (note that, in FIG. 35, the width of the white part is shown with a thickness greater than one pixel for the sake of description). Occurrence of such white streak data is assumed to be caused by a fault in the RIP process.

Conventionally, such white streak data is found at the time of checking (checking by eye) of print data by a proof or the like, for example. When white streak data is found, data before the RIP process is corrected or a parameter for execution of the RIP process is changed so that the white streak data will not be included in the print data. However, since such a conventional solution results in going-back in operation processes, the operation efficiency is low. Furthermore, changing a parameter for execution of the RIP process may result in a different fault. Moreover, if white streak data is caused but the white streak data is overlooked, this results in a so-called "print accident". It should be noted that the inventions disclosed in Japanese Laid-Open Patent Publication No. 2012-61759 and Japanese Laid-Open Patent Publication No. 2014-19016 are not aimed at detecting such white streak data. Even if a difference between pieces of data before and after RIP is detected by the printing system disclosed in Japanese Laid-Open Patent Publication No. 2014-19016, printing on a print sheet has to be performed to extract the difference, and going-back occurs in operation processes.

SUMMARY OF THE INVENTION

An object of the present invention is to provide a method (print data processing method) for enabling white streak data occurring due to a fault or the like in a RIP process to be easily detected. Furthermore, an additional object of the present invention is to provide a method of correcting the white steak data without causing going-back in operation processes or causing another fault.

To attain the above-described object, the present invention has features shown below.

One aspect of the present invention is directed to a print data processing method for processing print data obtained by performing a rasterization process on vector data, the method including:

a matching processing step of performing pattern matching between a streak detection pattern including a streak pattern having a width of one pixel and extending in a first direction or a second direction perpendicular to the first direction, and the print data;

a length measurement step of determining, when matching is established in the matching processing step, a length of a streak candidate part including a part corresponding to a streak pattern in a region where matching is established and a part continuous in an extending direction of the streak pattern and having a same value as a data value of the streak pattern, in the print data; and a determination step of determining whether or not the streak candidate part is streak data that possibly results in a streak, by comparing the length determined in the length measurement step against a predetermined threshold.

According to such a configuration, a pattern matching process which uses a streak detection pattern including a streak pattern having a width of one pixel is performed on print data obtained by performing a rasterization process on vector data (i.e. print data after RIP process). When matching is established in the pattern matching process, the length of a streak candidate part which is possibly the streak data is measured. Then, by comparing the length of the streak candidate part against a predetermined threshold, whether or not the streak candidate part is the streak data is determined. Due to such processing, unlike in the past, the streak data having a width of one pixel, which is unique data caused by a fault in the RIP process or the like, is easily detected.

Another aspect of the present invention is directed to a print data processing device for processing print data obtained by performing a rasterization process on vector data, the device including:

a matching processing unit configured to perform pattern matching between a streak detection pattern including a streak pattern having a width of one pixel and extending in a first direction or a second direction perpendicular to the first direction, and the print data;

a length measurement unit configured to determine, when matching is established by the pattern matching by the matching processing unit, a length of a streak candidate part including a part corresponding to a streak pattern in a region where matching is established and a part continuous in an extending direction of the streak pattern and having a same value as a data value of the streak pattern, in the print data; and a determination unit configured to determine whether or not the streak candidate part is streak data that possibly results in a streak, by comparing the length determined by the length measurement unit against a predetermined threshold.

A still another aspect of the present invention is directed to a computer-readable recording medium having recorded therein a print data processing program for processing print data obtained by performing a rasterization process on vector data, wherein the print data processing program causes a computer to perform:

a matching processing step of performing pattern matching between a streak detection pattern including a streak pattern having a width of one pixel and extending in a first direction or a second direction perpendicular to the first direction, and the print data;

a length measurement step of determining, when matching is established in the matching processing step, a length of a streak candidate part including a part corresponding to a streak pattern in a region where matching is established and a part continuous in an extending direction of the streak pattern and having a same value as a data value of the streak pattern, in the print data; and a determination step of determining whether or not the streak candidate part is streak data that possibly results in a streak, by comparing the length determined in the length measurement step against a predetermined threshold.

These and other objects, features, modes, and effects of the present invention will be made clear from the following detailed description of the present invention with reference to the accompanying drawings.

BRIEF DESCRIPTION OF THE DRAWINGS

FIG. 9 is a diagram showing a first streak detection pattern according to the first embodiment.

FIG. 10 is a diagram showing a second streak detection pattern according to the first embodiment.

FIG. 11 is a diagram for describing pattern matching according to the present embodiment.

FIG. 12 is a diagram showing an example of a record format of white streak data according to the first embodiment.

FIG. 13 is a diagram showing a state where the white streak data is stored in a white streak database according to the first embodiment.

DETAILED DESCRIPTION OF PREFERRED EMBODIMENTS

Hereinafter, preferred embodiments of the present invention will be described with reference to the drawings.

<1. First Embodiment>
<1.1 Overall Configuration of System>

Figure 1:
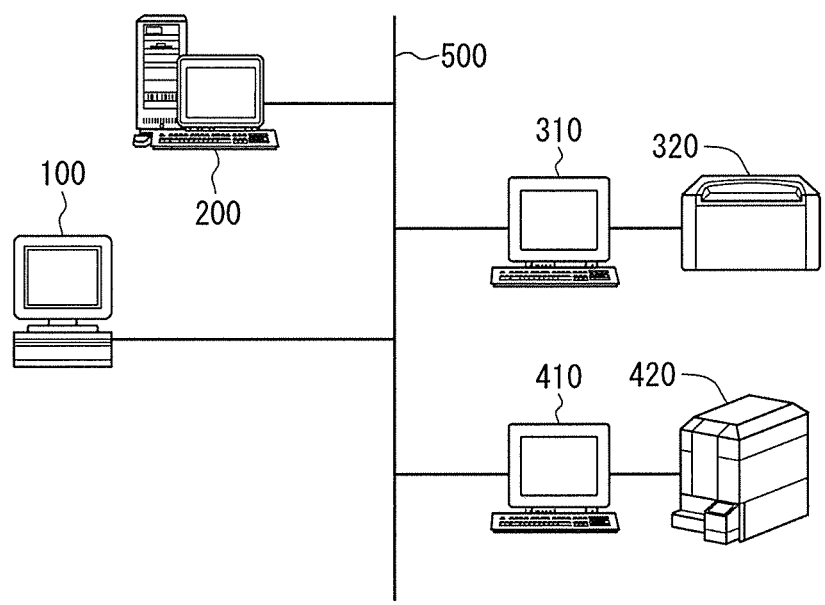
FIG. 1 is an overall configuration diagram of a printing system provided with a print data processing device according to a first embodiment of the present invention.

FIG. 1 is an overall configuration diagram of a printing system provided with a print data processing device 200 according to a first embodiment of the present invention. The printing system includes a client computer (computer referred to as "front-end") 100 for performing an edit process using characters, parts (logo, picture, illustration, etc.) and the like constituting a print material, a print data processing device 200 configured to perform data processing, such as a RIP process, on submitted data, a plate-making device 320, such as a plate recorder, and a controller 310 thereof, and a digital printer 420 and a controller 410 thereof. The client computer 100, the print data processing device 200, the controller 310 of the plate-making device 320, and the controller 410 of the digital printer 420 are communicably connected to one another by a communication line 500, such as a LAN. A configuration where the elements are not connected by a communication line may also be adopted.

Printing by the printing system is performed roughly in the following manner. First, by performing an edit operation, a layout operation or the like in the client computer 100, page data describing a print target by page description language or the like is generated. The page data generated by the client computer 100 is provided to the print data processing device 200 as submitted data. The print data processing device 200 performs data processing, such as the RIP process, on the submitted data. Print data which is bitmap data is thereby generated. At this time, bitmap data in a TIFF format of multi-value is generated by a rasterization process (rendering process) (RIP process in a narrow sense), and a halftone dot meshing process (screening process) is performed on the bitmap data in a TIFF format of multi-value, and bitmap data in a DotTIFF format (i.e. binary format) is thereby generated. Then, in the case where the print data is transmitted to the controller 310, a printing plate is made by the plate-making device 320 under the control of the controller 310. In the case where the print data is transmitted to the controller 410, printing is performed by the digital printer 420 under the control of the controller 410.

In the present embodiment, a process of detecting the white streak data described above (i.e. white streak detection process) is performed on the print data. Then, in the case where the white streak data is detected in the white streak detection process, a process of correcting the white streak data is performed as necessary. The corrected data is transmitted to the controller 310 or the controller 410, and thus, occurrence of a white streak in a printed material may be prevented. It should be noted that, in the following, the white streak detection process and the process of correcting the white streak data are collectively referred to as "print data processing" for the sake of convenience.

It should be noted that the print data processing may be performed on the bitmap data in a TIFF format of multi-value, which is data before the halftone dot meshing process, or on the bitmap data in a DotTIFF format, which is data after the halftone dot meshing process. In the present embodiment, it is assumed that the print data processing is performed on the bitmap data in a DotTIFF format.

Furthermore, in the present embodiment, it is assumed that print data used in the print data processing includes four pieces of color plate data (C-plate data, M-plate data, Y-plate data, and K-plate data). The data value of each pixel constituting each piece of color plate data is "1" or "0". In the following description, a pixel whose data value is "1" will be referred to as "black pixel", and a pixel whose data value is "0" as "white pixel".

<1.2 Configuration of Print Data Processing Device>

Figure 2:
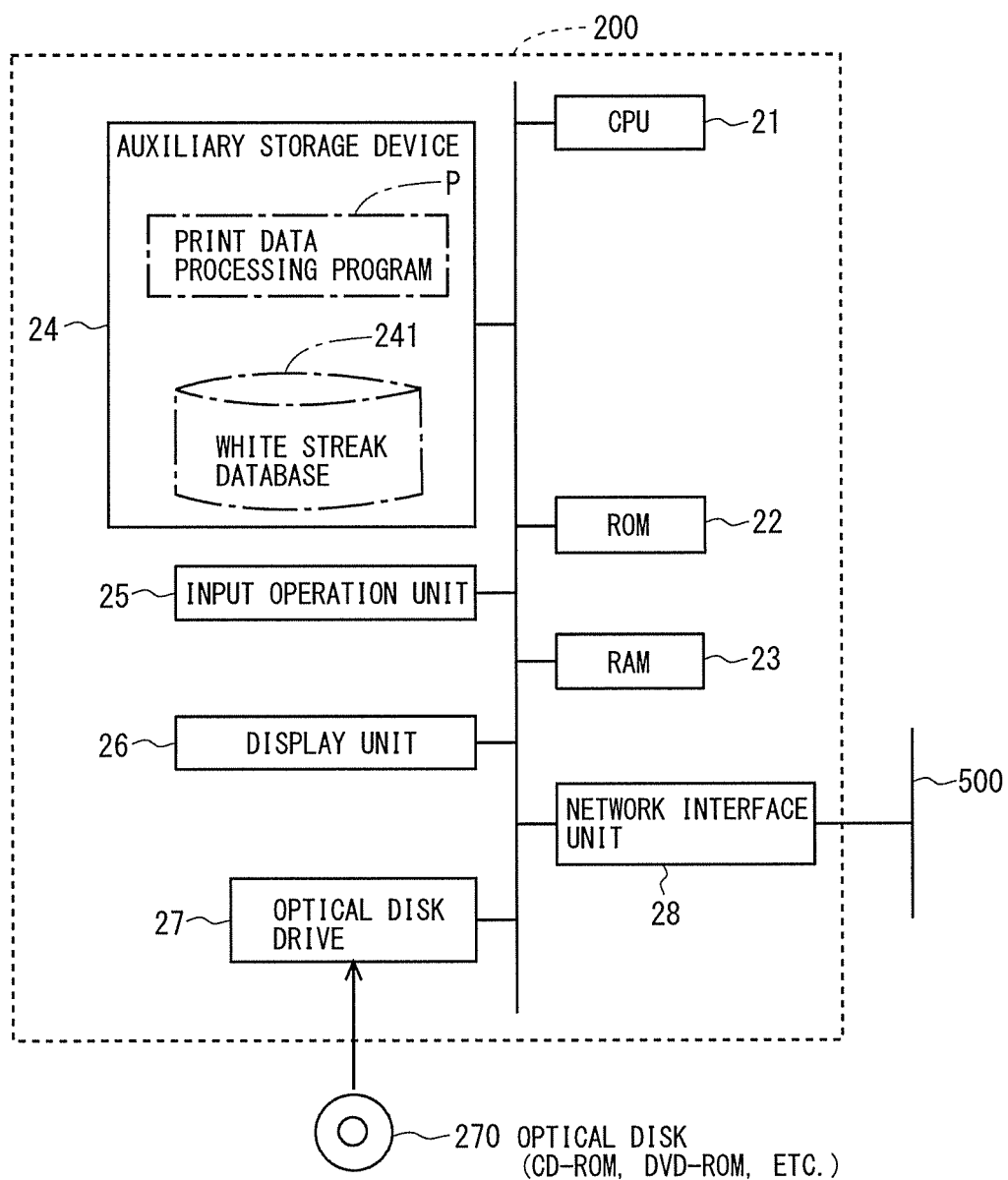
FIG. 2 is a hardware configuration diagram of the print data processing device according to the first embodiment.

FIG. 2 is a hardware configuration diagram of the print data processing device 200 according to the present embodiment. The print data processing device 200 is realized by a personal computer, and includes a CPU 21, a ROM 22, a RAM 23, an auxiliary storage device 24, an input operation unit 25 such as a keyboard, a display unit 26, an optical disk drive 27, and a network interface unit 28. The auxiliary storage device 24 is provided with a white streak database 241 configured to store the white streak data. The submitted data (page data) transmitted from the client computer 100 through the communication line 500 is inputted into the print data processing device 200 via the network interface unit 28. Print data which is generated by the print data processing device 200 based on the submitted data is transmitted to the controller 310 of the plate-making device 320 or the controller 410 of the digital printer 420 via the network interface 28 and through the communication line 500.

A program P for performing the print data processing according to the present embodiment (hereinafter such a program will be referred to as "print data processing program") is stored in the auxiliary storage device 24. When the print data processing device 200 is instructed to perform the print data processing, the print data processing program P is loaded into the RAM 23, and the print data processing program P loaded in the RAM 23 is executed by the CPU 21, and the print data processing is thereby executed. The print data processing program P is provided being stored in a computer-readable recording medium such as a CD-ROM or a DVD-ROM. That is, for example, a user purchases an optical disk (such as a CD-ROM or a DVD-ROM) 270 as a recording medium for the print data processing program P, attaches the optical disk 270 to the optical disk drive 27, and causes the print data processing program P to be read out from the optical disk 270 and to be installed in the auxiliary storage device 24. Alternatively, the print data processing program P transmitted through the communication line 500 may be received at the network interface unit 28, and be installed in the auxiliary storage device 24.

<1.3 Print Data Processing Method>
<1.3.1 Outline>

Figure 3:
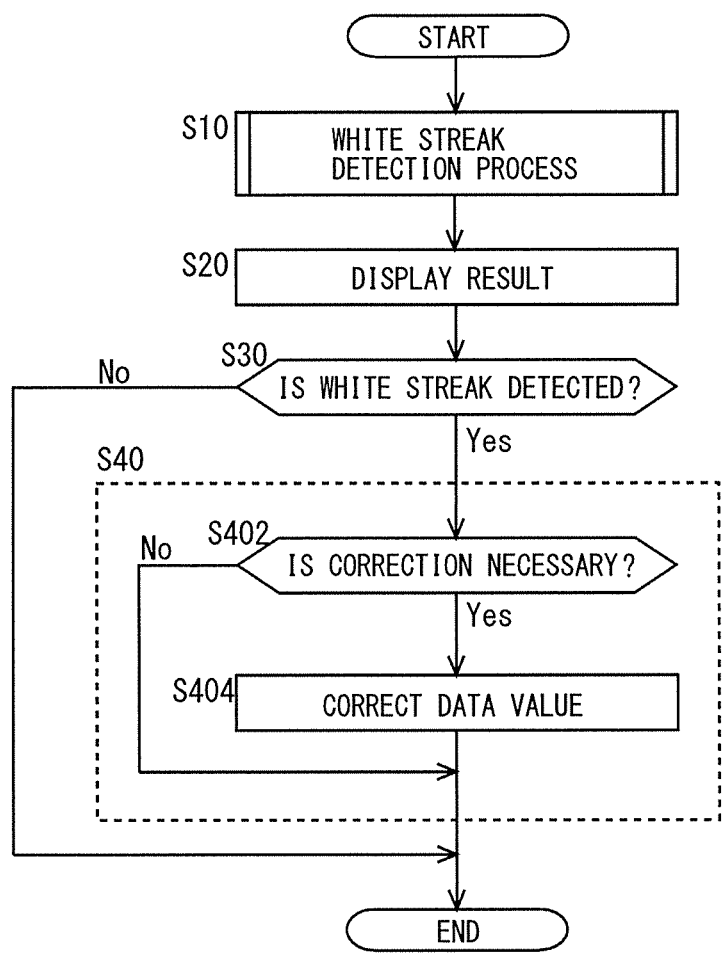
FIG. 3 is a flowchart showing a procedure of print data processing (processes for detection/correction of white streak data) according to the first embodiment.

FIG. 3 is a flowchart showing a procedure of the print data processing (processes for detection/correction of white streak data) according to the present embodiment. After the print data processing is started, first, the white streak detection process of detecting the white streak data is performed by using a technique of pattern matching or the like (step S10). Information about the white streak data, such as information regarding the position or the length, is thereby stored in the white streak database 241. In the present embodiment, the white streak detection process is performed for each plate (each piece of color plate data). It should be noted that a detailed description about the white streak detection process will be given later.

Figure 4:
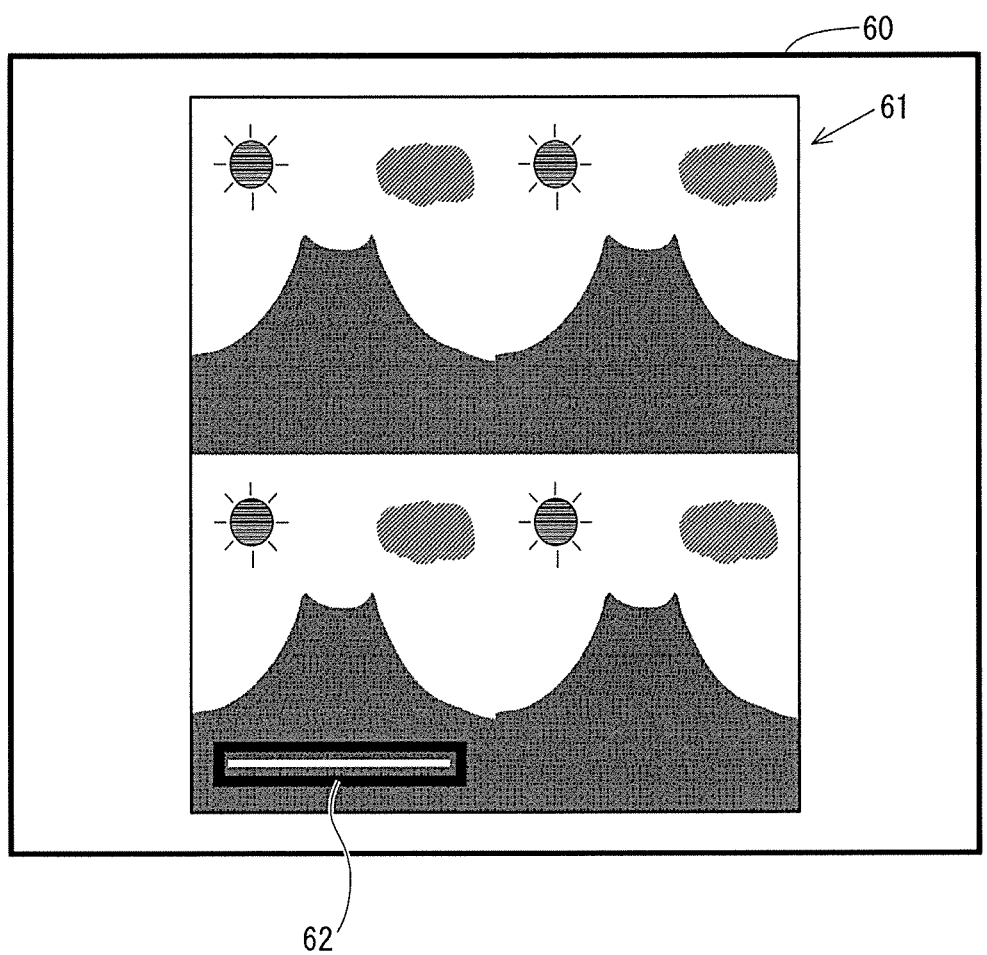
FIG. 4 is a diagram showing an example of a screen which is displayed as a result of a white streak detection process according to the first embodiment.

Next, a result of the white streak detection process is displayed on the display unit 26 of the print data processing device 200 by using the information stored in the white streak database 241 (step S20). In step S20, an image which is based on the print data is displayed in a mode emphasizing the white streak data detected in the white streak detection process so that the user is enabled to grasp the position of the white streak data. For example, an image as shown in FIG. 4 is displayed on the display unit 26. It should be noted that the example shown in FIG. 4 is an example where the same data is assigned to four sections by an imposition process, and where the white streak data is present only in a lower left section of the four sections. In this example, an image 61 which is based on the print data is displayed on a screen 60 displayed by image display software, and the white streak data is surrounded by a thick frame assigned with a reference sign "62" in the image 61. In step S20, the white streak data is displayed in an emphasized manner by being surrounded by such a thick frame, for example.

In the above manner, in step S20, an image which is based on the print data is displayed while highlighting the white streak data, as a result of the white streak detection process. It should be noted that, in the case where the white streak data is not detected in the white streak detection process, a screen indicating that the white streak data is not detected is displayed, for example.

Figure 5:
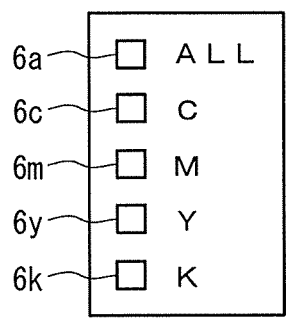
FIG. 5 is a diagram showing an example of a screen for receiving selection by a user for display/non-display of each piece of color plate data according to the first embodiment.
Figure 6:
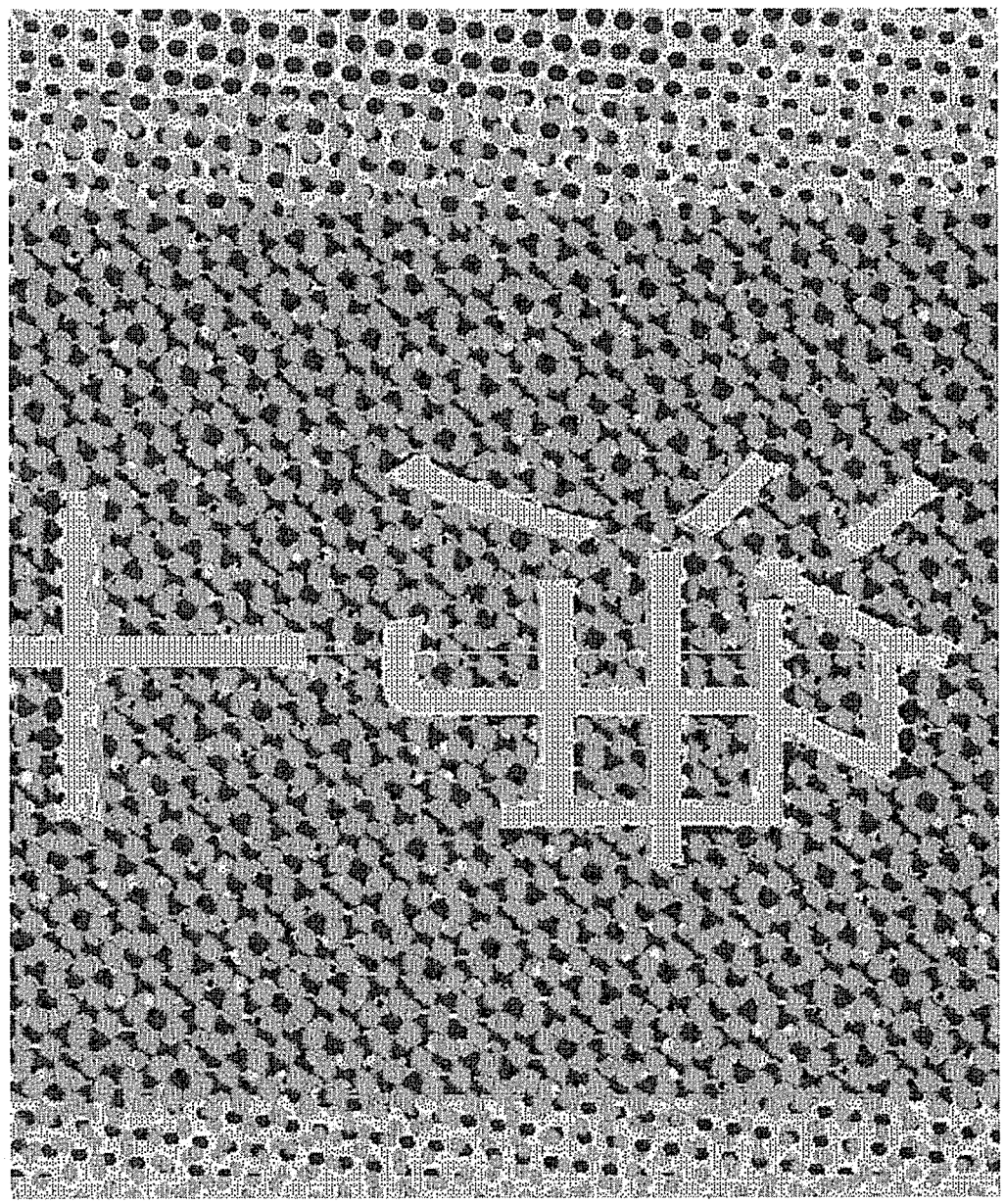
FIG. 6 is a diagram showing an example of an image that is displayed when all the pieces of color plate data are in a display state according to the first embodiment.
Figure 7:
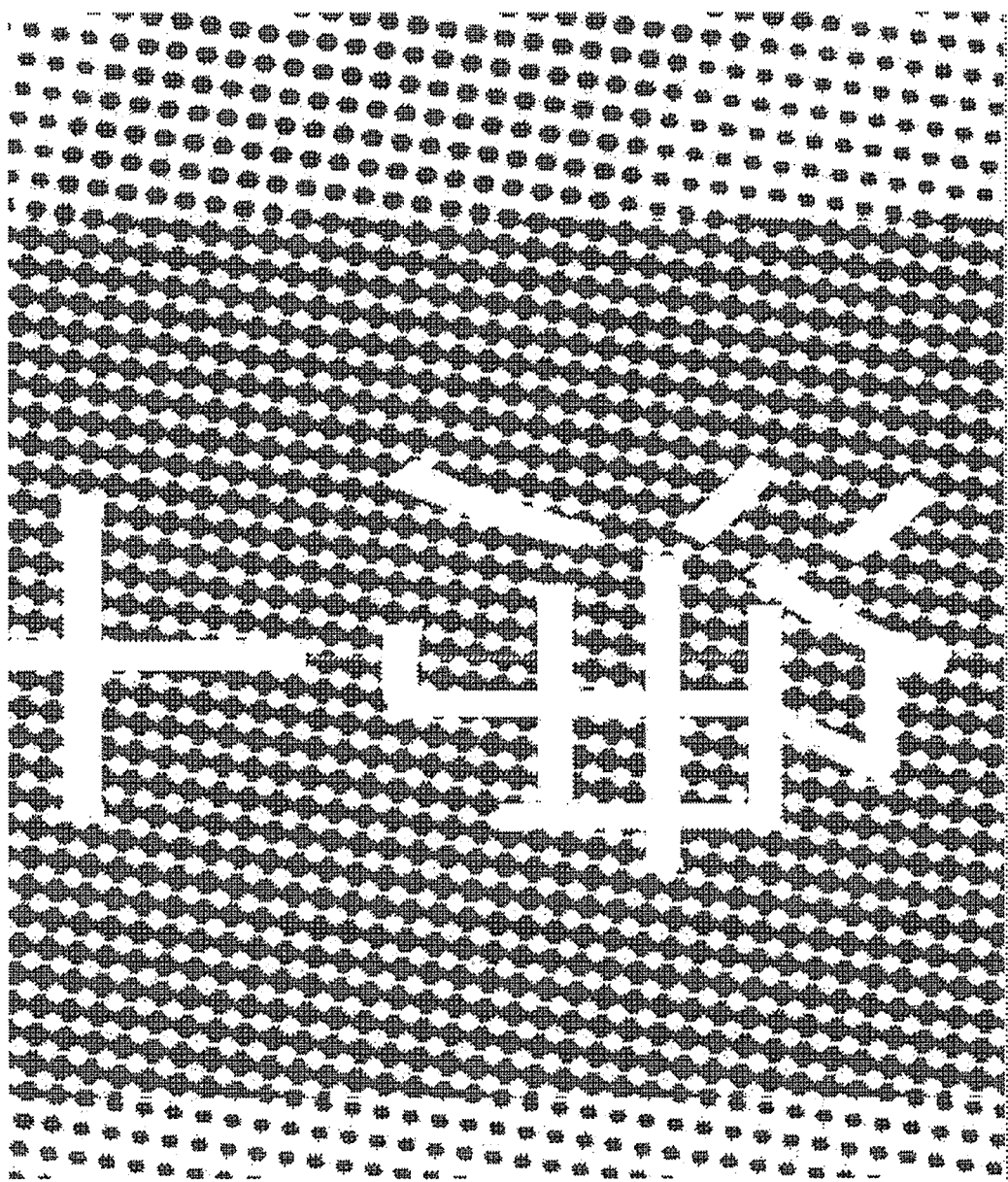
FIG. 7 is a diagram showing an example of an image that is displayed when only M-plate data is in the display state according to the first embodiment.

Moreover, in step S20, control of display/non-display may be performed for each piece of color plate data by user operation at the time of display of the image based on the print data. Since the print data includes four pieces of color plate data (C-plate data, M-plate data, Y-plate data, and K-plate data) in the present embodiment as described above, selection of display/non-display of each piece of color plate data by a user may be received by displaying a screen as shown in FIG. 5, for example. Five check boxes 6a, 6c, 6m, 6y, and 6k are provided on the screen shown in FIG. 5. Display/non-display is switched for each piece of color plate data by switching the check box 6c, 6m, 6y, 6k between an on state and an off state. Furthermore, when the check box 6a is switched to the on state, all the pieces of color plate data are switched to a display state, and when the check box 6a is switched to the off state, all the pieces of color plate data are switched to a non-display state. Because display/non-display can be controlled in the above manner, an image as shown in FIG. 7 may be displayed by switching only the M-plate data to the display state in a case where an image as shown in FIG. 6 is displayed when all the pieces of color plate data are in the display state, for example. Accordingly, a RIP process result for a part where the white streak data is present may be easily checked.

After step S20, when the white streak data is detected in the white streak detection process, the process proceeds to step S40, and when the white streak data is not detected in the white streak detection process, the print data processing is ended (step S30).

In step S40, a process of correcting the white streak data is performed. In the present embodiment, step S40 includes step S402 and step S404. In step S402, whether or not data correction is necessary for the white streak data detected in the white streak detection process (step S10) is determined by the user. When data correction is determined to be necessary, the process proceeds to step S404. On the other hand, when data correction is determined to be not necessary, the print data processing is ended. In step S404, a data value of the white streak data is corrected. Printing is thereby performed based on print data after correction of the white streak data, and occurrence of a white streak in a printed material may be prevented. It should be noted that a detailed description of correction of the white streak data will be given later. When correction of the white streak data is finished, the print data processing is ended.

It should be noted that, in the present embodiment, a streak detection result display step is realized by step S20, and a correction step is realized by step S40.

<1.3.2 White Streak Detection Process>

Next, the white streak detection process (FIG. 3, step S10) will be described in detail.

<1.3.2.1 Processing Procedure>

Figure 8:
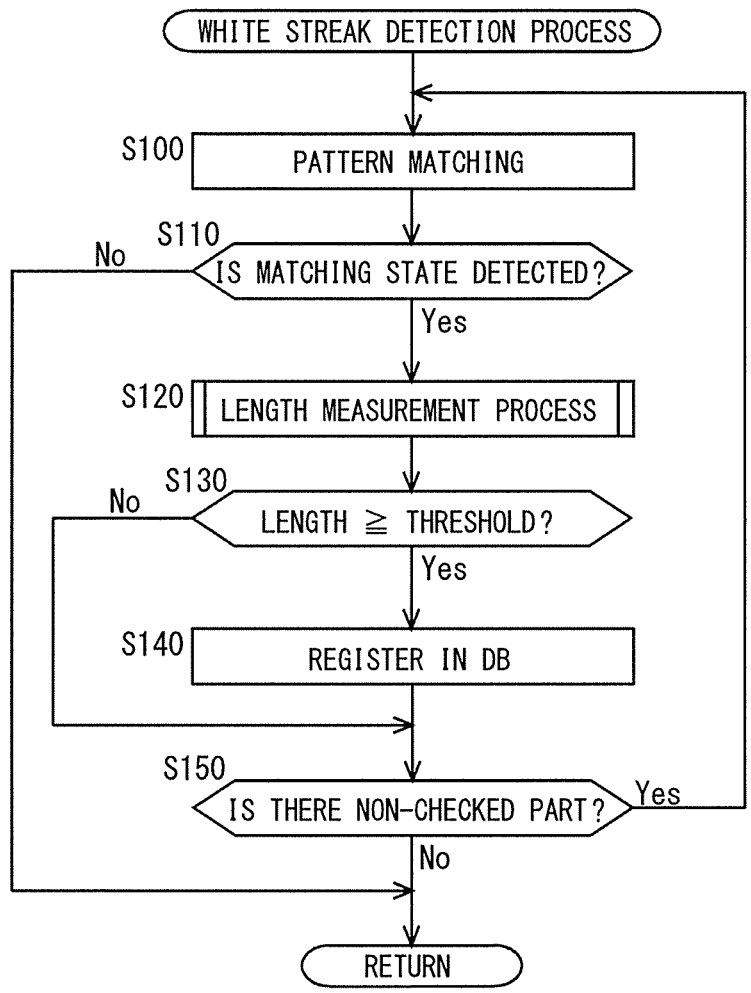
FIG. 8 is a flowchart showing a procedure of the white streak detection process according to the first embodiment.

FIG. 8 is a flowchart showing a procedure of the white streak detection process. It should be noted that, in the present embodiment, the processing shown in FIG. 8 is performed for each plate (each piece of color plate data). After the white streak detection process is started, first, pattern matching is performed between a streak detection pattern which is prepared in advance and the print data (step S100). In the present embodiment, a first streak detection pattern for detecting white streak data extending in an X-axis direction, and a second streak detection pattern for detecting white streak data in a Y-axis direction are prepared. FIG. 9 is a diagram showing the first streak detection pattern, and FIG. 10 is a diagram showing the second streak detection pattern. As can be seen in FIGS. 9 and 10, the streak detection pattern in the present embodiment includes 9 pixels of "3 vertical pixels×3 horizontal pixels". As shown in FIG. 9, regarding the first streak detection pattern, all the pixels in a second row are white pixels, and all the pixels in first and third rows are black pixels. Moreover, as shown in FIG. 10, regarding the second streak detection pattern, all the pixels in a second column are white pixels, and all the pixels in first and third columns are black pixels. White streak data having a width of one pixel can be detected by using such a streak detection pattern. In the following, a part (pattern), of the streak detection pattern, formed from a plurality of continuous white pixels, such as the second row of the first streak detection pattern or the second column of the second streak detection pattern, will be referred to as "streak pattern". It should be noted that patterns other than those shown in FIGS. 9 and 10 may also be used as the streak detection pattern as long as the white streak data can be detected. For example, the first streak detection pattern may be constituted from 15 pixels of "3 vertical pixels×5 horizontal pixels" where all the pixels in the second row are white pixels and all the pixels in the first and third rows are black pixels.

In step S100, pattern matching is performed on the entire print data by using the streak detection patterns as described above. Details will be given with reference to FIG. 11. Here, it is assumed that coordinates are assigned to each pixel constituting the print data, as shown in FIG. 11. For example, an X-coordinate is "2" and a Y-coordinate is "3" for a pixel assigned with a reference sign "64". In step S100, pattern matching using the first streak detection pattern and pattern matching using the second streak detection pattern have to be performed. Here, it is assumed that pattern matching using the first streak detection pattern is performed first.

In the first step S100 after start of the white streak detection process, it is checked whether or not matching is established in a state where a top left pixel of the first streak detection pattern is positioned at a pixel at coordinates (1, 1) of the print data (that is, it is checked whether or not the data values of all the 9 pixels coincide between the first streak detection pattern and the print data). Next, the check is performed in a state where the top left pixel of the first streak detection pattern is positioned at a pixel at coordinates (2, 1) or (4, 1) of the print data. The check is performed in this manner by sequentially moving the first streak detection pattern in the right direction until pixels on a right end of the first streak detection pattern are positioned at pixels on a right end of the print data. Then, the check is performed in a state where the top left pixel of the first streak detection pattern is positioned at a pixel at coordinates (1, 2) of the print data. Next, the check is performed in a state where the top left pixel of the first streak detection pattern is positioned at a pixel at coordinates (2, 2) or (4, 2) of the print data. The check is sequentially performed in this manner until a bottom right pixel of the first streak detection pattern is positioned at a bottom right pixel of the print data. Pattern matching using the first streak detection pattern is performed in this manner on the entire print data. Then, pattern matching using the second streak detection pattern is performed in the same manner on the entire print data.

However, in the process of one step S100 in FIG. 8, if matching is established at a certain position by the check, the pattern matching process is temporarily stopped at this position. That is, when a matched state is detected, the process proceeds to step S120 (step S110). Meanwhile, when pattern matching using the second streak detection pattern is finished for the entire print data, the white streak detection process is ended (step S110). In the case where the process returns to step S100 by determination in step S150 described later, the check is sequentially performed in the above manner for non-checked parts.

In step S120, a process (length measurement process) of determining a length of a white streak candidate part, which is a candidate part for the white streak data, is performed. A white streak candidate part refers to, more specifically, a plurality of continuous pixels (in this case, white pixels) including a part corresponding to a streak pattern in a region where matching is established and a part continuous in the extending direction of the streak pattern and having a same value as the data value (in this case, "0") of the streak pattern, in the print data. It should be noted that a detailed description of the length measurement process will be given later.

After the length measurement process is ended, whether or not the length of the white streak candidate part is equal to or greater than a predetermined threshold is determined (step S130). When the length of the white streak candidate part is equal to or greater than the predetermined threshold, the process proceeds to step S140, and when the length of the white streak candidate part is less than the predetermined threshold, the process proceeds to step S150. It should be noted that, when the length of the white streak candidate part is equal to or greater than the predetermined threshold, this white streak candidate part is treated as the white streak data.

In step S140, the white streak candidate part whose length is determined to be equal to or greater than the predetermined threshold in step S130 is registered in the white streak database 241 as the white streak data. FIG. 12 is a diagram showing an example of a record format of the white streak data. As shown in FIG. 12, attributes of the white streak data include start coordinates, end coordinates, a length, and a direction. For example, the white streak data is stored in the white streak database 241 as schematically shown in FIG. 13. It should be noted that, in the example shown in FIG. 13, with respect to direction, the X-axis direction is represented by "0", and the Y-axis direction is represented by "1".

Figure 14:
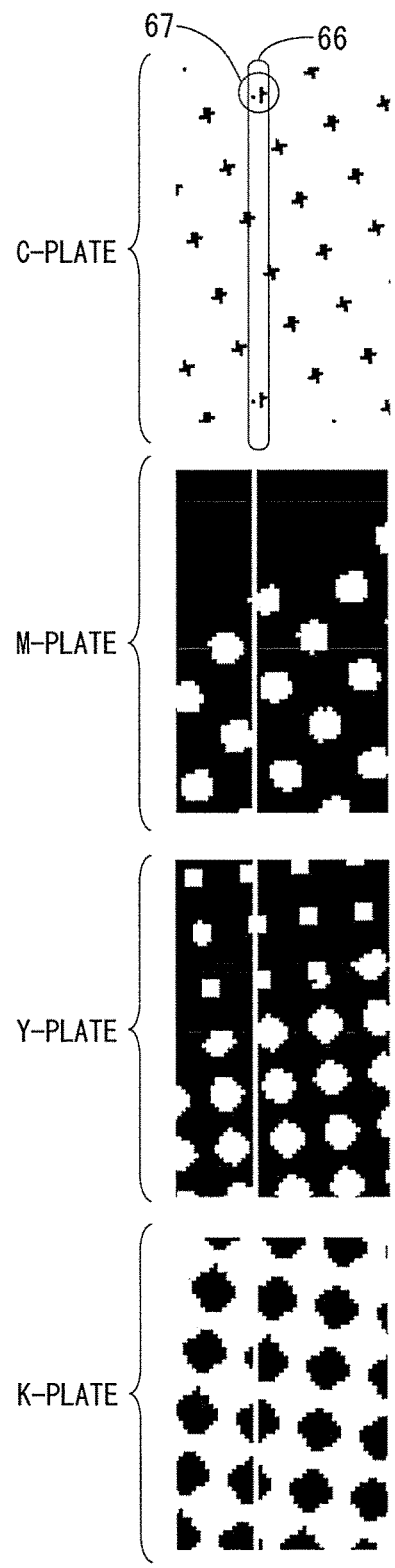
FIG. 14 is a diagram for describing a reason for sharing the white streak database according to the first embodiment.
Figure 15:
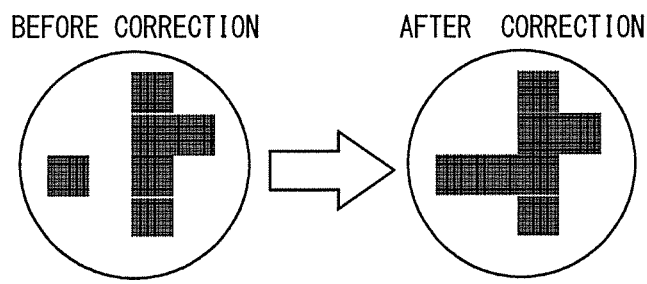
FIG. 15 is a diagram for describing a reason for sharing the white streak database according to the first embodiment.

Although the white streak detection process is performed for each plate (each piece of color plate data) as described above, the white streak database 241 is shared by all the plates. The reason for sharing the white streak database 241 is as follows. Determination of whether or not the white streak data is included in the print data is performed based on data of each plate (i.e. color plate data). Accordingly, the result of the white streak detection process may be different for each plate. For example, in the case where the print data includes four pieces of color plate data as shown in FIG. 14, the white streak data can be detected from the M-plate data, the Y-plate data, and the K-plate data, but the white streak data cannot be detected from the C-plate data. This is because, in the case of this example, data values of most part of the C-plate data indicated by a reference sign "66" in FIG. 14 are "0". In such a case, if data correction (FIG. 3, step S40) is performed without sharing the white streak database 241 (that is, if correction of each piece of color plate data is performed based only on the result of the white streak detection process for the respective piece of color plate data), data correction is not performed for the C-plate data because the white streak data is not detected for the C-plate data. Accordingly, with respect to a part indicated by a reference sign "67" in FIG. 14, although data correction should be performed in the manner shown in FIG. 15, such correction is not performed. Therefore, in the present embodiment, the white streak database 241 is shared by all the plates so that desired correction is performed also on such data as described in this example. Correction of a piece of color plate data based on the result of the white streak detection process for another plate may thus be performed.

In step S150, whether or not a part which is not yet checked by pattern matching remains in the print data is determined. When there is a non-checked part, the process returns to step S100. On the other hand, when there is no part which is not yet checked, the white streak detection process is ended.

It should be noted that, in the present embodiment, a matching processing step is realized by step S100, a length measurement step is realized by step S120, and a determination step is realized by step S130.

<1.3.2.2 Length Measurement Process>

Next, the length measurement process (FIG. 8, step S120) will be described in detail. In the length measurement process, measurement of the length of a white streak candidate part as described above is performed. Measurement of the length is performed with reference to a position where matching is established by pattern matching. It should be noted that, although an example will be described for measurement of the length of a white streak candidate part extending in the X-axis direction, the same will apply to measurement of the length of a white streak candidate part extending in the Y-axis direction.

Figure 16:
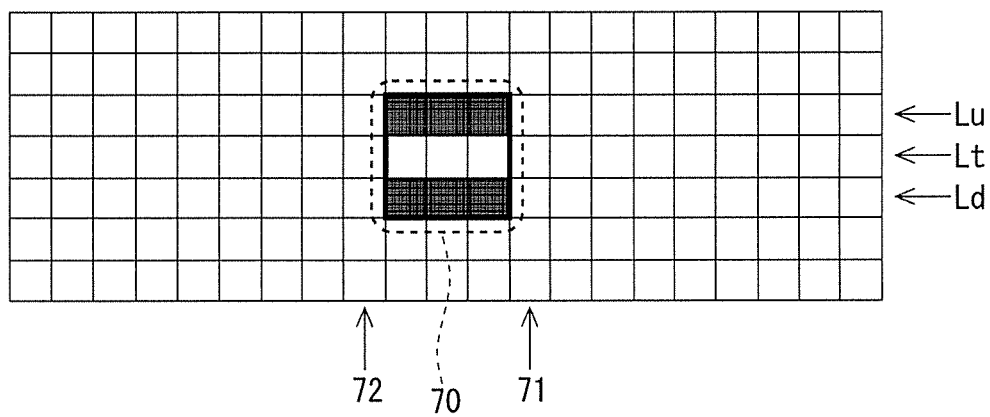
FIG. 16 is a diagram for describing a length measurement process according to the first embodiment.

Terms used in the description of the length measurement process will be described. Focusing on a white streak candidate part extending in the X-axis direction, matching is assumed to be established at a part assigned with a reference sign "70" in FIG. 16. At this time, since the white streak candidate part is present in a line including the part corresponding to a streak pattern in the aforementioned part (part indicated by the reference sign "70"), the line will be referred to as "check target line". Furthermore, a line adjacent to the check target line on an upper side will be referred to as "upper-side target line", and a line adjacent to the check target line on a lower side will be referred to as "lower-side target line". The check target line is assigned with a reference sign "Lt", the upper-side target line with a reference sign "Lu", and the lower-side target line with a reference sign "Ld".

Figure 17:
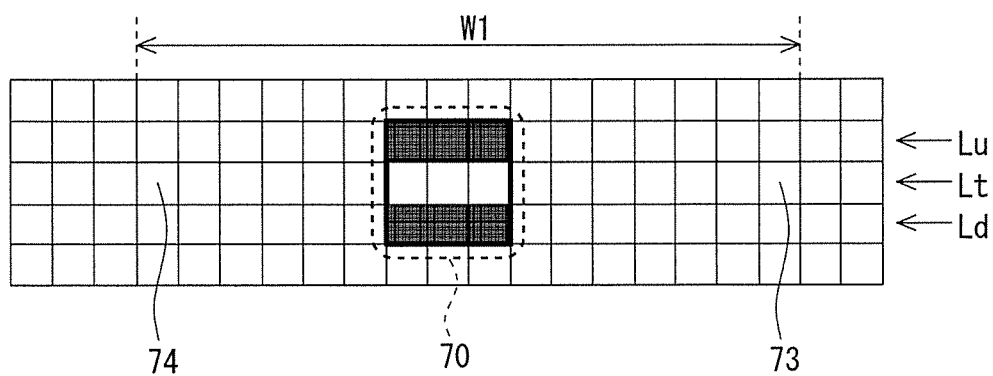
FIG. 17 is a diagram for describing the length measurement process according to the first embodiment.

Measurement of the length is performed in both a right direction and a left direction of the part where matching is established. At this time, data values of pixels are checked on a per column basis from columns which are adjacent on the left and right of the part where matching is established (i.e. columns assigned with reference signs "71", "72" in FIG. 16) towards end portions of the print data. Then, when at least one of two conditions described later is satisfied, measurement of the length in the direction being checked is ended. As a result, for example, when it is determined by measurement in the right direction that pixels up to a pixel assigned with a reference sign "73" in FIG. 17 are included in the white streak candidate part, and it is determined by measurement in the left direction that pixels up to a pixel assigned with a reference sign "74" in FIG. 17 are included in the white streak candidate part, the length of the white streak candidate part is the length of an arrow assigned with a reference sign "W1" in FIG. 17 (i.e. a value obtained by multiplying a horizontal length of a pixel by the number of pixels from the pixel 73 to the pixel 74). It should be noted that, in the following, columns that are adjacent on the left and right of a part where matching is established will be referred to as "check start column(s)".

In the following, the two conditions (first condition and second condition) for ending measurement of the length in each direction will be described. It should be noted that, although measurement in the right direction will be described as an example, the same will apply to measurement in the left direction.

Figure 18:
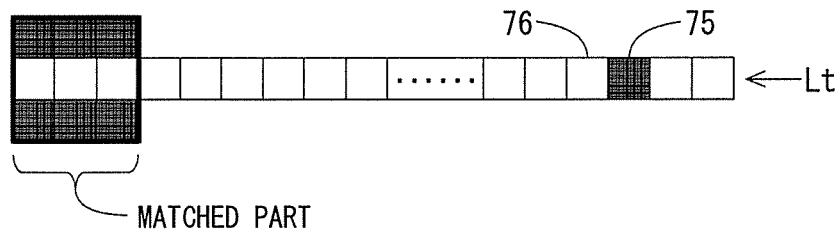
FIG. 18 is a diagram for describing a first condition for ending measurement of a length according to the first embodiment.
Figure 19:
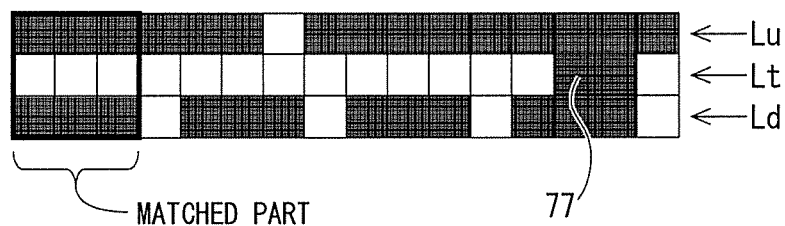
FIG. 19 is a diagram for describing the first condition for ending measurement of a length according to the first embodiment.

First, the first condition will be described. Data values are sequentially checked for the check target line Lt on a per pixel basis in the right direction from a pixel in the check start column 71. Then, measurement of the length in the right direction is ended when a pixel whose data value is "1" (i.e. black pixel) is detected. For example, data on the right side of the streak pattern in the part where matching is established is assumed to be data as shown in FIG. 18. At this time, the first condition is satisfied when the data value of a pixel assigned with a reference sign "75" is checked. In this case, pixels up to a pixel assigned with a reference sign "76" are included in the white streak candidate part. Furthermore, when data on the right side of the part where matching is established is data as shown in FIG. 19, the first condition is satisfied when the data value of a pixel assigned with a reference sign "77" is checked.

Figure 20:
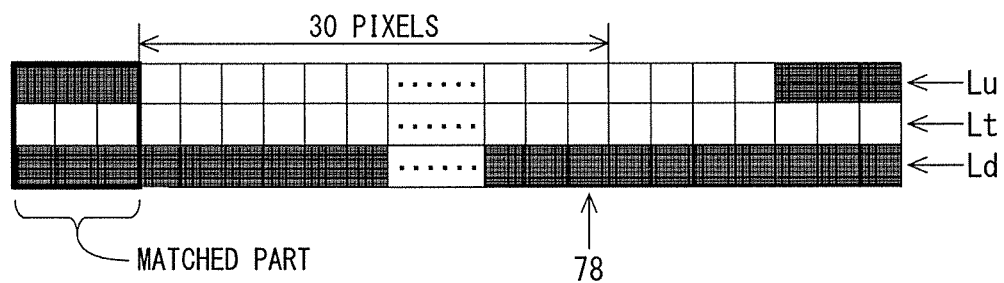
FIG. 20 is a diagram for describing a second condition for ending measurement of a length according to the first embodiment.

Next, the second condition will be described. Data values are sequentially checked for each of the upper-side target line Lu and the lower-side target line Ld on a per pixel basis in the right direction from a pixel in the check start column 71. Then, measurement of the length in the right direction is ended when there are a predetermined number of continuous pixels whose data values are "0" (i.e. white pixels) in at least one of the upper-side target line Lu and the lower-side target line Ld. More specifically, measurement of the length in the right direction is ended when a 'state where three pixels whose data values are "0" lie next to each other' consecutively occurs a predetermined times in at least one of upper-side target line Lu and the lower-side target line Ld. For example, it is assumed that, in the case where setting is performed such that measurement of the length is ended when the corresponding state occurs ten times in succession, the data on the right side of the part where matching is established is data as shown in FIG. 20. At this time, the second condition is satisfied when the data value of a pixel in a column assigned with a reference sign "78" in FIG. 20 is checked for the upper-side target line Lu. It should be noted that the reason the second condition is set as described above is that, in a case where there are a large number of continuous white pixels in the upper-side target line Lu or the lower-side target line Ld, the check target line Lt is considered to also naturally include continuous white pixels (i.e. white pixels are continuous not because of a fault in the RIP process or the like).

Figure 21:
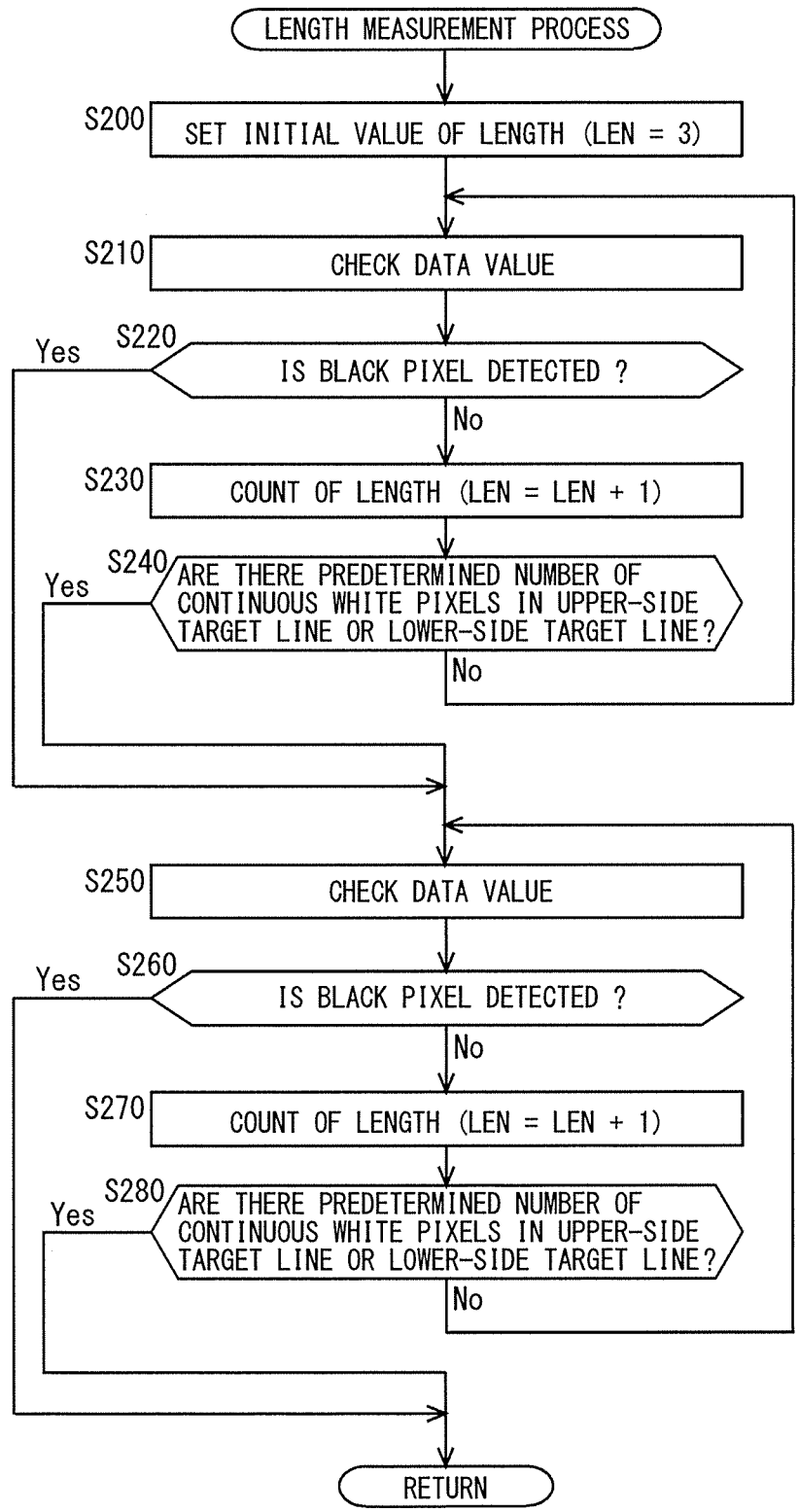
FIG. 21 is a flowchart showing a procedure of the length measurement process according to the first embodiment.

Based on the description given above, a procedure of the length measurement process will be described with reference to the flowchart shown in FIG. 21. It should be noted that, other than the two conditions described above, measurement of the length is also ended when a target pixel whose data value is checked reaches an end portion of the print data. However, such a case is not shown in FIG. 21. Moreover, although an example will be described for measurement of the length of a white streak candidate part extending in the X-axis direction, the same will apply to measurement of the length of a white streak candidate part extending in the Y-axis direction.

After the length measurement process is started, first, a variable LEN for length measurement is set to an initial value (step S200). In the present embodiment, since a streak pattern includes three white pixels, the variable LEN is set to three. It should be noted that, in this case, the length is determined on the premise that the width of each pixel is normalized to one. Accordingly, the value of a length which is determined in this length measurement process is equal to the number of pixels forming the white streak candidate part.

Next, the data value of a pixel in a check target column is checked for each of the check target line Lt, the upper-side target line Lu, and the lower-side target line Ld (step S210). Regarding this, in the process in first step S210, the check start column 71 described above (see FIG. 16) corresponds to the check target column, and in the process in second or later step S210, a column which is adjacent on the right of the column which was checked immediately before corresponds to the check target column.

Next, whether or not a black pixel is detected is determined (that is, whether or not the second condition is satisfied is determined) based on the result of the check in step S210 (step S220). As a result, when a black pixel is detected (that is, when the data value of a pixel in the check target line Lt is "1"), the process proceeds to step S250. On the other hand, when a black pixel is not detected, the process proceeds to step S230. In step S230, one is added to the variable LEN. A pixel being checked is thus included in the white streak candidate part.

In step S240, whether or not a predetermined number of continuous white pixels are present in the upper-side target line Lu or the lower-side target line Ld is determined (that is, whether or not the first condition is satisfied is determined) based on the result of the check in step S210. As a result, when a predetermined number of continuous white pixels are present in the upper-side target line Lu or the lower-side target line Ld, the process proceeds to step S250. On the other hand, when a predetermined number of continuous white pixels are not present in both the upper-side target line Lu and the lower-side target line Ld, the process returns to step S210.

It should be noted that the reason why the step of counting the length (step S230) is provided between step S220 and step S240 is that, while the pixel in a column being checked is not included in the white streak candidate part when the first condition is satisfied by the check in step S210, the pixel in a column being checked is included in the white streak candidate part when the second condition is satisfied by the check in step S210.

Measurement of the length in the right direction of a part where matching is established is performed by repeating the processes from steps S210 to S240 in the above manner. Then, measurement of the length in the left direction of the part where matching is established is performed by repeating the processes from step S250 to S280 in the same manner as steps S210 to S240.

Figure 22:
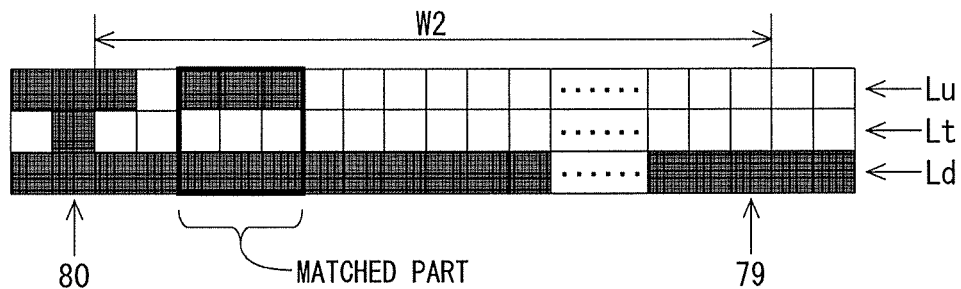
FIG. 22 is a diagram for describing a length of a white streak candidate part according to the first embodiment.

According to the processing as described above, when the print data is data as shown in FIG. 22, length measurement in the right direction is ended, for example, when a column assigned with a reference sign "79" is checked, and length measurement in the left direction is ended when a column assigned with a reference sign "80" is checked. Thus, the value indicating the length of the white streak candidate part is the number of pixels in one row in a range indicated by an arrow assigned with a reference sign "W2" in FIG. 22 (because the length is determined here on the premise that the width of each pixel is normalized to one).

It should be noted that the procedure described above is only an example, and the present invention is not limited thereto. For example, in the case where a pixel in a column being checked at the time of satisfaction of the second condition is not to be included in the white streak candidate part, the process in step S240 may be performed between the process in step S220 and the process in step S230, and the process in step S280 may be performed between the process in step S260 and the process in step S270.

<1.3.3 Correction of White Streak Data (FIG. 3, step S404)>

Next, a method of correcting the white streak data will be described. It should be noted that, although the focus is on the white streak data extending in the X-axis direction also in this case, correction of the white streak data extending in the Y-axis direction is performed in the same manner.

Figure 23:
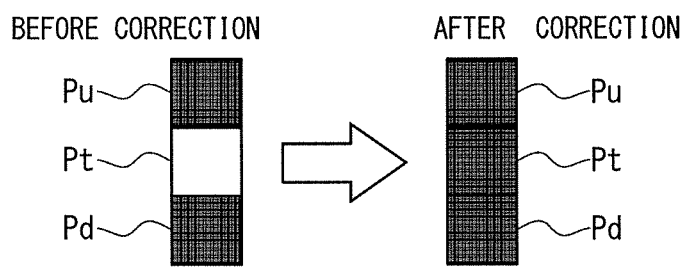
FIG. 23 is a diagram for describing correction of the white streak data according to the first embodiment.
Figure 24:
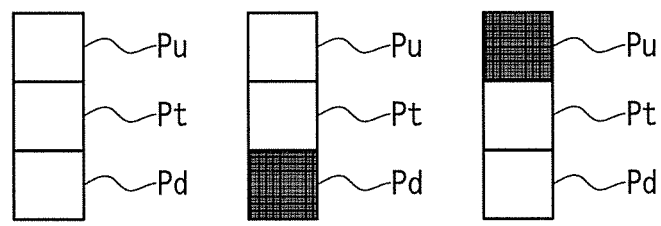
FIG. 24 is a diagram for describing correction of the white streak data according to the first embodiment.

While the white streak data is configured by a plurality of pixels, correction of a data value is performed on a per pixel basis. Specifically, when each pixel constituting the white streak data is defined as "target pixel", if both a pixel Pu which is adjacent on the top of a target pixel Pt and a pixel Pd which is adjacent on the bottom of the target pixel Pt are black pixels, the target pixel Pt is corrected from a white pixel to a black pixel (that is, the data value of the target pixel Pt is corrected from "0" to "1"), as shown in FIG. 23. In other words, in the case where the data values of the two pixels Pu, Pd adjacent to the target pixel Pt in a direction perpendicular to the extending direction of the white streak data are values (in this case, "1") different from the data value of the streak pattern (in this case, "0"), the data value of the target pixel Pt is corrected to a value (in this case, "1") different from the data value of the streak pattern (in this case, "0"). On the other hand, in the case where at least one of the pixel Pu and the pixel Pd is a white pixel (that is, in the case where the pattern of the data values is one of the patterns shown in FIG. 24), the target pixel Pt remains as a white pixel (that is, the data value of the target pixel Pt is not corrected).

Figure 25:
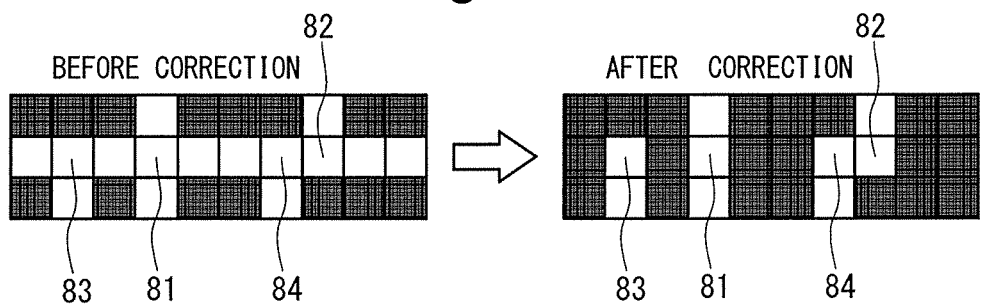
FIG. 25 is a diagram for describing correction of the white streak data according to the first embodiment.

From the above, the white streak data is thereby corrected in the manner shown in FIG. 25, for example. In the example shown in FIG. 25, both a pixel which is adjacent on the top and a pixel which is adjacent on the bottom are white pixels with respect to a pixel assigned with a reference sign "81", a pixel which is adjacent on the top is a white pixel with respect to a pixel assigned with a reference sign "82", and a pixel which is adjacent on the bottom is a white pixel with respect to each of pixels assigned with reference signs "83", "84". Accordingly, when focusing on pixels constituting the white streak data, the pixels assigned with the reference signs "81" to "84" remain as white pixels, and other pixels are corrected from white pixels to black pixels.

<1.4 Effects>

According to the present embodiment, a pattern matching process which uses a streak detection pattern including a streak pattern having a width of one pixel is performed on print data which has been subjected to the RIP process. When matching is established in the pattern matching process, by checking data values of pixels in the print data sequentially in the extending direction of the streak pattern from a part where matching is established, a white streak candidate part which is possibly the white streak data is specified and the length of the white streak candidate part is measured. Then, by comparing the length of the white streak candidate part against a predetermined threshold, whether or not the white streak candidate part is the white streak data is determined. Due to such processing, unlike in the past, the white streak data having a width of one pixel, which is unique data caused by a fault in the RIP process or the like, is easily detected. Furthermore, in the case where the white streak data is detected, correction of the white streak data is performed as appropriate with respect to the print data after the RIP process. Accordingly, a user can obtain print data not including the white streak data, without having to perform a task of correcting data before the RIP process or a task of changing a parameter and re-executing the RIP process.

As described above, according to the present embodiment, a user can easily detect the white streak data which is caused due to a fault in the RIP process or the like. Furthermore, when the white streak data is included in print data after the RIP process, the white streak data can be corrected without causing going-back in operation processes or causing another fault. As a result, occurrence of a so-called "print accident" is prevented.

<1.5 Modification>

<1.5.1 First Modification>

In the first embodiment described above, a description is given on the premise that the print data processing (processes for detection/correction of white streak data) is performed on data in a DotTIFF format. However, the present invention is not limited thereto. The print data processing may be performed on data in a TIFF format of multi-value, as in a present modification. Unique aspects of the present modification will be described below.

Figure 26:
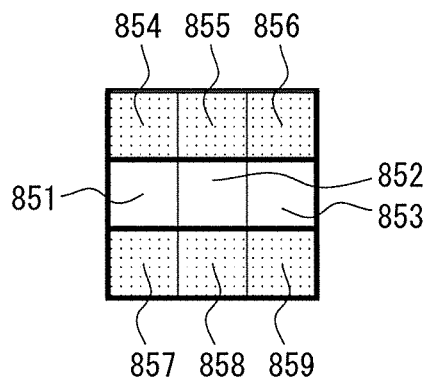
FIG. 26 is a diagram for describing a streak detection pattern according to a first modification of the first embodiment.

With respect to data in a TIFF format of multi-value, data of one pixel includes 32 bits (8 bits for each color), for example. Accordingly, in the present modification, a streak detection pattern different from that in the first embodiment is used. It should be noted that, in this case, the focus is on a streak detection pattern which is used for detection of white streak data extending in the X-axis direction. Also in the present modification, the streak detection pattern includes 9 pixels of "3 vertical pixels×3 horizontal pixels", as shown in FIG. 26. With respect to this streak detection pattern, a 'state where all the 32 bits are "0"' is assigned to all the pixels in a second row (pixels assigned with reference signs "851" to "853"), and a 'state other than a state where all the 32 bits are "0"' is assigned to all the pixels in first and third rows (pixels assigned with reference signs "854" to "859"). Then, pattern matching is performed in the same manner as in the first embodiment, by using such a streak detection pattern. It should be noted that, in the present modification, pieces of data of all the plates are collected as one piece of data in a TIFF format of multi-value. Accordingly, the white streak detection process (see FIG. 8) including the pattern matching process is performed on one piece of data in a TIFF format of multi-value, unlike in the first embodiment where the white streak detection process is performed for each plate.

Also with respect to the length measurement process (see FIG. 21), at the time of checking the data value of each pixel, the 'state where all the 32 bits are "0"' in the present modification is associated with "0" in the first embodiment, and the 'state other than a state where all the 32 bits are "0"' in the present modification is associated with "1" in the first embodiment. The same process as in the first embodiment is performed on such a premise.

In the present modification, correction of the white streak data is performed in the following manner. When each pixel constituting the white streak data is defined as "target pixel", if the data values of both a pixel which is adjacent on the top of the target pixel and a pixel which is adjacent on the bottom of the target pixel are the 'state other than a state where all the 32 bits are "0"', the data value of the target pixel is corrected. Two techniques described below (first technique and second technique) are conceivable as the specific technique of correction.

Figure 27:
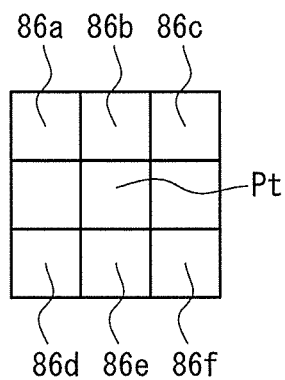
FIG. 27 is a diagram for describing a first technique regarding correction of the white streak data according to the first modification of the first embodiment.

According to the first technique, the data value of the target pixel is corrected to an average value of the data values of pixels around the target pixel. More specifically, since a pixel which is adjacent on the left of the target pixel and a pixel which is adjacent on the right of the target pixel are in the 'state where all the 32 bits are "0"' in the case where the streak data extends in the X-axis direction as in this example, the data value of the target pixel is corrected to the average value of the data values of six pixels assigned with reference signs "86a" to "86f" in FIG. 27.

Figures 28, 29:
FIG. 28 is a diagram for describing a second technique regarding correction of the white streak data according to the first modification of the first embodiment.
FIG. 29 is a diagram for describing an outline of a second embodiment of the present invention.

According to the second technique, the data value of the target pixel is corrected to a value calculated by a filtering process performed using the data values of pixels around the target pixel. A known technique may be used for the filtering process. For example, the filtering process may be performed by using a filter as shown in FIG. 28. In the example shown in FIG. 28, a filter coefficient for two pixels which are adjacent on the top and bottom of the target pixel Pt is two-eighths, and a filter coefficient for four pixels which are diagonally above and left, diagonally above and right, diagonally below and left, and diagonally below and right of the target pixel Pt is one-eighth. When the filtering process is performed using such a filter, the data value of the target pixel is corrected to a sum value of values obtained by multiplying the data values of surrounding pixels by respective filter coefficients.

It should be noted that, in addition to the two techniques described above, it is conceivable to correct the data value of the target pixel to an average value of the data value of a pixel which is adjacent on the top of the target pixel and the data value of a pixel which is adjacent on the bottom of the target pixel, or to correct the data value of the target pixel to one of the data value of the pixel which is adjacent on the top of the target pixel and the data value of the pixel which is adjacent on the bottom of the target pixel.

In the above manner, also in the case where the print data processing (processes for detection/correction of white streak data) is performed on data in a TIFF format of multi-value, the white streak data which is caused due to a fault in the RIP process or the like can be easily detected, and the white streak data can be corrected without causing going-back in operation processes or causing another fault.

<1.5.2 Second Modification>

In the first embodiment described above, with respect to the white streak data detected in the white streak detection process, a data value is actually corrected only when correction of data is determined to be necessary by a user. Regarding this, correction of the data value is performed on only one pixel width portion, and correction of the data value of the target pixel is performed based on the data values of surrounding pixels. Accordingly, even when correction of the data value is performed for all the pieces of white streak data detected in the white streak detection process, the print result is considered to be not greatly negatively affected.

Accordingly, in the present modification, correction of the data value is automatically performed for all the pieces of white streak data detected in the white streak detection process, without providing a step which is performed by a user to determine whether correction of data is necessary or not. That is, the process in step S402 in the flowchart shown in FIG. 3 is not performed. In this manner, in the present modification, the data value of white streak data detected in the white streak detection process is corrected, without receiving an instruction from outside, in the print data processing device 200.

According to the present modification, the operation burden of a user in the case where white streak data is included in print data after the RIP process can be reduced.

<2. Second Embodiment>
<2.1 Outline>

A second embodiment of the present invention will be described. In the first embodiment, a check based on pattern matching is performed on the entire print data. Accordingly, there is a concern that the time required for the check (FIG. 8, step S100) becomes long. Therefore, in the present embodiment, a technique which enables the time required for the check based on pattern matching to be reduced than in the first embodiment is adopted.

Regarding this, when focusing on white streak data extending in the X-axis direction, data of a line including the white streak data (hereinafter referred to as "white streak line") and lines which are adjacent on the top and bottom of the line (hereinafter such lines will be simply referred to as "adjacent lines") is as shown in FIG. 29, for example. As can be seen in FIG. 29, a total value of the data values of pixels in the white streak line and a total value of the data values of pixels in the adjacent line are greatly different. Accordingly, in the present embodiment, the total value of the data values of pixels in each line and the total value of the data values of pixels in the adjacent line thereof are compared against each other, and the check based on pattern matching is performed only on a part where the difference is great. In the following, aspects different from those in the first embodiment will be described.

<2.2 Print Data Processing Method>

Figure 30:
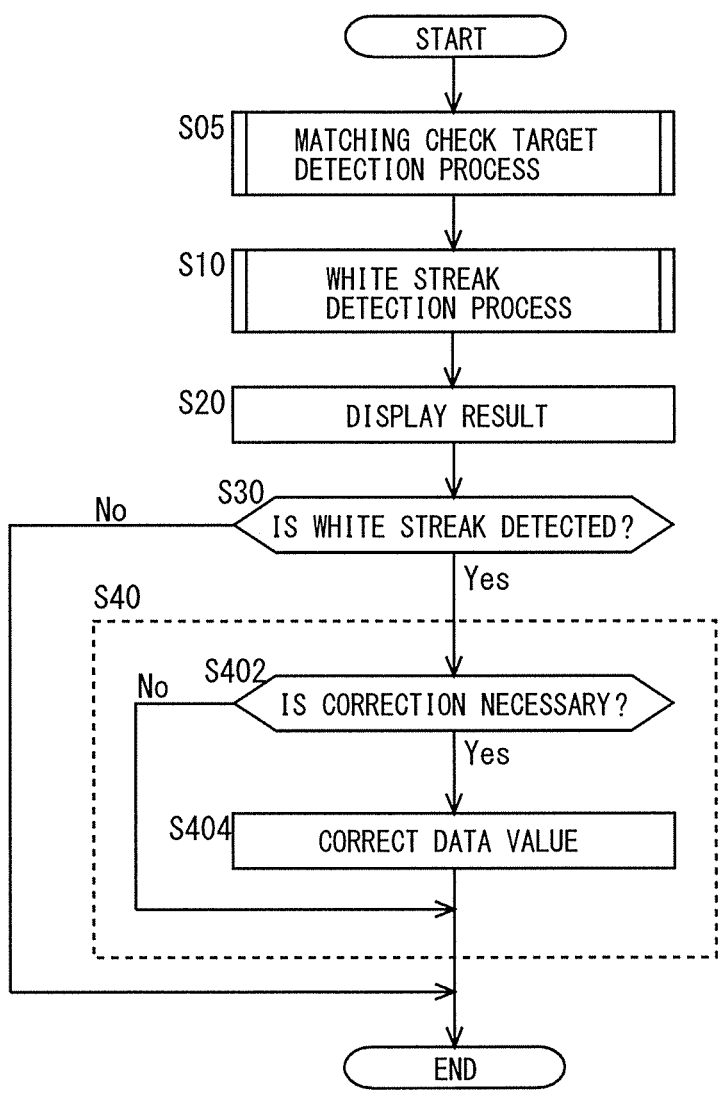
FIG. 30 is a flowchart showing a procedure of print data processing (processes for detection/correction of white streak data) according to the second embodiment.

FIG. 30 is a flowchart showing a procedure of print data processing (processes for detection/correction of white streak data) according to the present embodiment. In the present embodiment, after the print data processing is started, first, a matching check target detection process (step S05) of detecting a part where pattern matching is to be performed in the white streak detection process (step S10) is performed. In the following, the matching check target detection process will be described.

Figure 31:
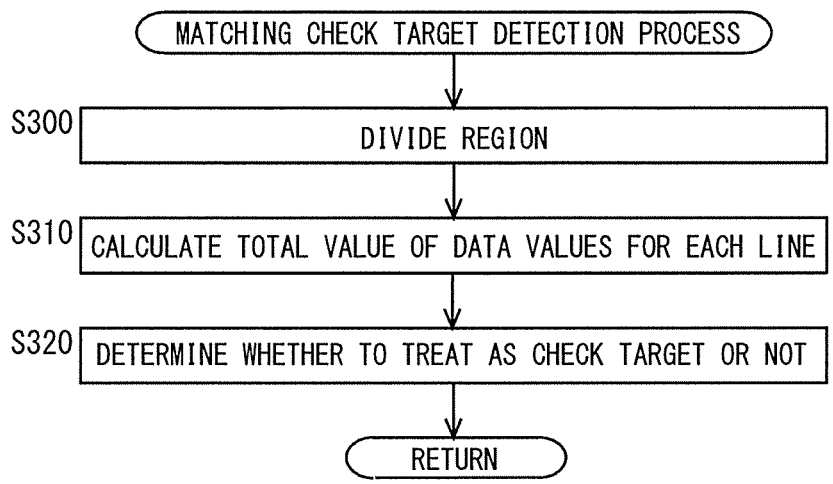
FIG. 31 is a flowchart showing a procedure of a matching check target detection process according to the second embodiment.
Figure 32:
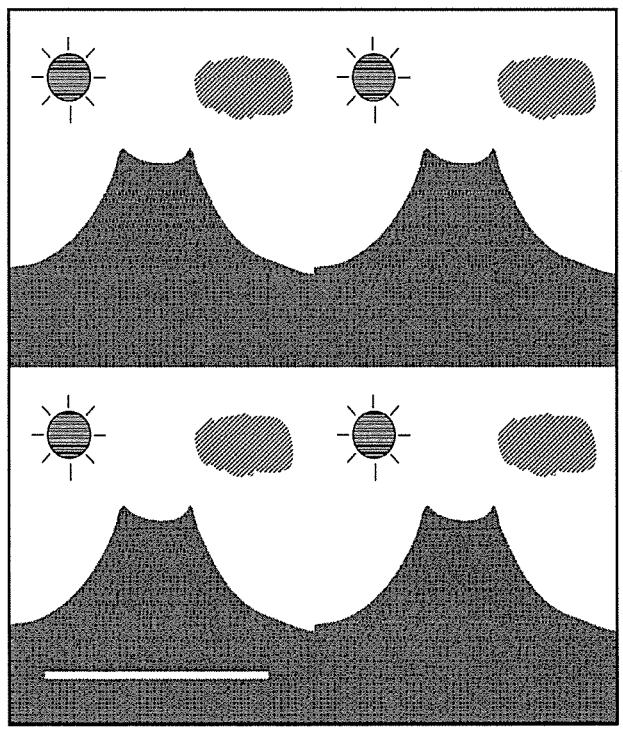
FIG. 32 is a diagram for describing division of a region according to the second embodiment.
Figure 33:
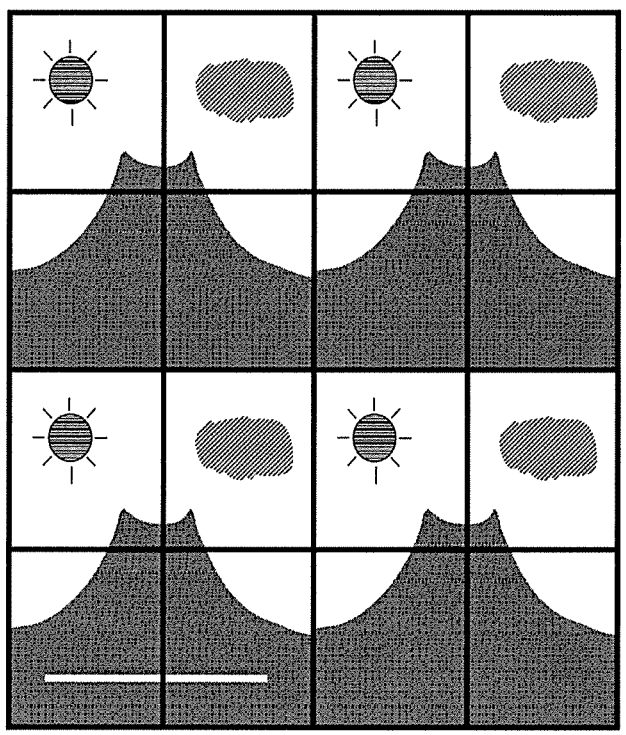
FIG. 33 is a diagram for describing division of a region according to the second embodiment.

FIG. 31 is a flowchart showing a procedure of the matching check target detection process. After the matching check target detection process is started, first, a region of the entire print data is divided into a predetermined number of regions (step S300). Due to this step S300, for example, print data as shown in FIG. 32 is divided into a plurality of regions as shown in FIG. 33 (where the borders of the regions are indicated by thick frames). It should be noted that, in the example shown in FIG. 33, the region of the entire print data is divided into 16 regions. The reason for performing such region division is that, if region division is not performed, the total value of the data values of each line becomes too great in step S310 described later, and an error tends to occur in the determination result in step S320 described later.

Next, the total value of the data values is calculated for each line in each region (step S310). Then, a determination is made as to whether or not each line is to be made a check target of pattern matching is performed based on the values calculated in step S310 (step S320). More specifically, in step S320, each line is taken as a processing target line in turn, and a line group including the processing target line and two lines which are adjacent to the processing target line is determined to be a matching check target, when a difference between the total value of the data values of the processing target line and the total value of the data values of a line which is adjacent on one side of the processing target line is equal to or greater than a predetermined threshold, and a difference between the total value of the data values of the processing target line and the total value of the data values of a line which is adjacent on the other side of the processing target line is equal to or greater than the predetermined threshold.

Figure 34:
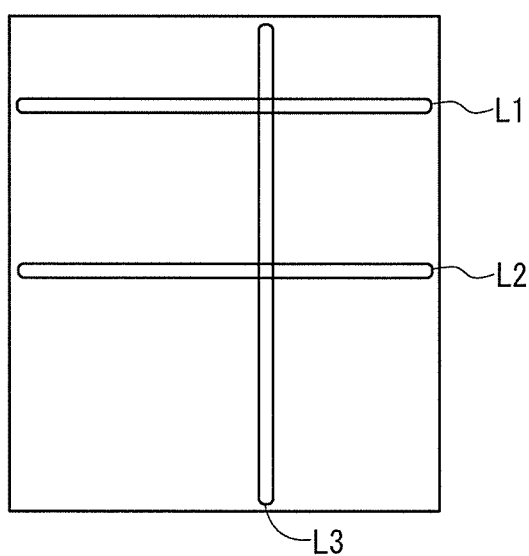
FIG. 34 is a diagram for describing a check by pattern matching according to the second embodiment.
Figure 35:
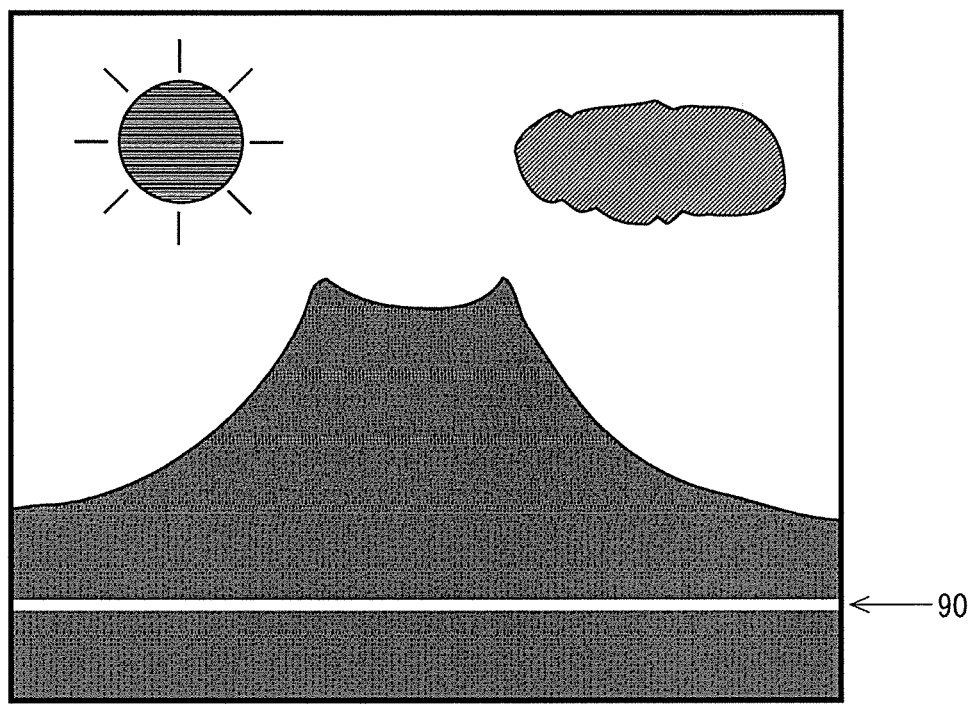
FIG. 35 is a diagram for describing the white streak data.

When step S320 is ended, the white streak detection process (FIG. 30, step S10) is performed. While a check based on pattern matching is performed in this white streak detection process (see FIG. 8), in the present embodiment, the check is performed only on a part which is determined in the matching check target detection process described above to be a matching check target. For example, when parts assigned with reference signs "L1" to "L3" in FIG. 34 are determined in the matching check target detection process to be matching check targets, the check based on pattern matching is performed only on these parts. Other processes are the same as those in the first embodiment.

<2.3 Effects>

Also in the present embodiment, the same effects as those of the first embodiment are obtained. Furthermore, according to the present embodiment, the time required for detection of the white streak data can be reduced than in the first embodiment.

The present invention has been described in detail, but the description given above is exemplary in every aspect, and is not restrictive. Various other changes and modifications are conceivable within the scope of the present invention.

It should be noted that the present application claims priority based on Japanese Patent Application No. 2017-032884 titled "Print Data Processing Method, Print Data Processing Device, and Print Data Processing Program" filed on Feb. 24, 2017, the content of which is incorporated herein by reference.

What is claimed is:

1. A print data processing method for processing print data obtained by performing a rasterization process on vector data, the method comprising:
   a matching processing step of performing pattern matching between a streak detection pattern including a streak pattern having a width of one pixel and extending in a first direction or a second direction perpendicular to the first direction, and the print data;
   a length measurement step of determining, when matching is established in the matching processing step, a length of a streak candidate part including a part corresponding to a streak pattern in a region where matching is established and a part continuous in an extending direction of the streak pattern and having a same value as a data value of the streak pattern, in the print data;
   a determination step of determining whether or not the streak candidate part is streak data that possibly results in a streak, by comparing the length determined in the length measurement step against a predetermined threshold; and
   a correction step of correcting a data value of each pixel constituting the streak data, based on a data value of a neighboring pixel, wherein
   the print data is binary bitmap data, and
   in the correction step, each pixel constituting the streak data is made a target pixel in turn, and a data value of a target pixel is corrected to a value different from a data value of the streak pattern, when data values of two pixels that are adjacent to the target pixel in a direction perpendicular to the extending direction of the streak data are different from the data value of the streak pattern.

2. A print data processing method for processing print data obtained by performing a rasterization process on vector data, the method comprising:
   a matching processing step of performing pattern matching between a streak detection pattern including a streak pattern having a width of one pixel and extending in a first direction or a second direction perpendicular to the first direction, and the print data;
   a length measurement step of determining, when matching is established in the matching processing step, a length of a streak candidate part including a part corresponding to a streak pattern in a region where matching is established and a part continuous in an extending direction of the streak pattern and having a same value as a data value of the streak pattern, in the print data;
   a determination step of determining whether or not the streak candidate part is streak data that possibly results in a streak, by comparing the length determined in the length measurement step against a predetermined threshold; and
   a correction step of correcting a data value of each pixel constituting the streak data, based on a data value of a neighboring pixel, wherein
   the print data is multi-valued bitmap data, and
   in the correction step, the data value of each pixel constituting the streak data is corrected to a value that is calculated by a filtering process that is performed by using data values of surrounding pixels.

3. The print data processing method according to claim 2, wherein, in the correction step, the data value of each pixel constituting the streak data is corrected to an average value of data values of surrounding pixels.

4. A print data processing method for processing print data obtained by performing a rasterization process on vector data, the method comprising:
   a matching processing step of performing pattern matching between a streak detection pattern including a streak pattern having a width of one pixel and extending in a first direction or a second direction perpendicular to the first direction, and the print data;
   a length measurement step of determining, when matching is established in the matching processing step, a length of a streak candidate part including a part corresponding to a streak pattern in a region where matching is established and a part continuous in an extending direction of the streak pattern and having a same value as a data value of the streak pattern, in the print data;

a determination step of determining whether or not the streak candidate part is streak data that possibly results in a streak, by comparing the length determined in the length measurement step against a predetermined threshold; and a streak detection result display step of displaying an image based on the print data while emphasizing the streak data.

5. The print data processing method according to claim 4, wherein the print data includes a plurality of pieces of color plate data, and in the streak detection result display step, control of display/non-display can be performed for each piece of color plate data at a time of displaying the image based on the print data.

6. A print data processing device for processing print data obtained by performing a rasterization process on vector data, the device comprising:

a processor; and a memory storing programs, the programs, which when executed by the processor, cause the processor to function as:

a matching processing unit configured to perform pattern matching between a streak detection pattern including a streak pattern having a width of one pixel and extending in a first direction or a second direction perpendicular to the first direction, and the print data;

a length measurement unit configured to determine, when matching is established by the pattern matching by the matching processing unit, a length of a streak candidate part including a part corresponding to a streak pattern in a region where matching is established and a part continuous in an extending direction of the streak pattern and having a same value as a data value of the streak pattern, in the print data;

a determination unit configured to determine whether or not the streak candidate part is streak data that possibly results in a streak by comparing the length determined by the length measurement unit against a predetermined threshold; and a result display unit configured to display a screen indicating that the streak data is not detected when the streak data is not detected by the determination unit, and to display an image so that a user is enabled to grasp the position of the streak data in the image when the streak data is detected by the determination unit.

* * * * *